United States Patent [19]

Sendlak

[11] 4,129,602

[45] Dec. 12, 1978

[54] LIQUID PHASE FLUORINATION PROCESS

[75] Inventor: Lawrence P. Sendlak, Tonawanda, N.Y.

[73] Assignee: Hooker Chemicals & Plastics Corp., Niagara Falls, N.Y.

[21] Appl. No.: 829,846

[22] Filed: Sep. 1, 1977

[51] Int. Cl.² ............................................. C07C 25/04
[52] U.S. Cl. ............................ 260/651 F; 260/650 F; 260/653.7
[58] Field of Search ............. 260/649 F, 650 F, 653.7, 260/651 F

[56] References Cited

U.S. PATENT DOCUMENTS

| | | | |
|---|---|---|---|
| 2,058,453 | 10/1936 | Holt et al. | 260/653.7 |
| 2,062,743 | 12/1936 | Dandt et al. | 260/651 F |
| 2,993,937 | 7/1961 | Paulath | 260/650 F |
| 3,131,226 | 4/1964 | Olstowski et al. | 260/653.8 |
| 3,136,822 | 6/1964 | Fraimier | 260/651 |
| 3,149,170 | 9/1964 | Clark et al. | 260/653.4 |
| 3,183,276 | 5/1965 | Vecchio | 260/653.4 |
| 3,258,500 | 6/1966 | Swamer et al. | 260/653.7 |
| 3,287,424 | 11/1966 | Pacini et al. | 260/651 |
| 3,426,009 | 2/1969 | Chapman et al. | 260/653.7 |
| 3,431,067 | 3/1969 | Kato et al. | 23/88 |
| 3,435,082 | 3/1969 | Ager | 260/653.8 |
| 3,742,074 | 6/1973 | Hermann et al. | 260/651 F |
| 3,755,477 | 8/1973 | Firth et al. | 260/653.4 |
| 3,950,445 | 4/1976 | Ryf | 260/651 F |
| 4,022,717 | 5/1977 | Clement | 260/2 H |
| 4,079,089 | 3/1978 | Klauke | 260/651 F |

FOREIGN PATENT DOCUMENTS

| | | | |
|---|---|---|---|
| 1313588 | 11/1962 | France | 260/651 F |
| 17373/65 | 6/1965 | Japan | 260/651 F |

OTHER PUBLICATIONS

Tewksbury et al., JACS, 71, pp. 2336–2337, Jul. 1949.

Primary Examiner—C. Davis
Attorney, Agent, or Firm—Peter F. Casella; William J. Crossetta, Jr.; Arthur S. Cookfair

[57] ABSTRACT

A process for the preparation of compounds of the formula

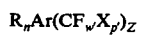

comprises contacting compounds of the formula

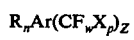

in the liquid phase, with hydrogen fluoride in the presence of a catalyst selected from the group consisting of pentachloride and pentafluoride of tantalum, niobium and rhenium.

Ar is aryl;
R is a substituent on the aryl nucleus selected from the group consisting of aryl, substituted aryl, halogen, alkyl, alkoxy, and substituted alkyl;
n is 0 to 9;
X is halogen atom other than fluorine;
w is 0 to 2;
p is 1 to 3;
w' is 1 to 3, and is greater than w;
p' is 0 to 2, and is less than p;
w + p is 3;
w' + p' is 3;
Z is 1–10; and
the maximum value of n + Z is 10.

22 Claims, No Drawings

LIQUID PHASE FLUORINATION PROCESS

BACKGROUND OF THE INVENTION

This invention relates to a process for the preparation of organic fluoride compounds, and in particular, to a process for the liquid phase replacement of halogen atoms with fluorine in organic compounds.

A variety of fluorination processes are known wherein fluorine replaces one or more halogen substituents of a halogenated organic compound. Such known processes include both vapor phase fluorination reaction and liquid phase fluorination reactions. Typically, such processes involve the reaction of a halocarbon compound with a fluorination agent, sometimes in the presence of catalyst, such as antimony pentachloride, at atmospheric or super-atmospheric pressures. Many of the known processes, while suitable for laboratory investigations and experiments, are unsuitable for commercial use for various reasons, such as the low purity or yield of product, the need for containment of high pressures, the high cost of equipment which must be employed, or the need for frequent replacement of the catalyst, due to loss or deactivation. One of the common difficulties encountered in vapor phase fluorination reactions results from the highly exothermic nature of such reactions. The heat evolved frequently results in a temperature rise sufficient to cause thermal decomposition of some of the organic starting materials and a resultant carbonization of the catalyst. Furthermore, such vapor phase reactions commonly require the use of substantial stoichiometric excess of hydrogen fluoride with the attendant problem of disposal of the hazardous hydrogen fluoride containing effluent gases.

Some of the problems associated with vapor phase fluorination processes may be avoided through the use of liquid phase fluorination. However, although atmospheric liquid phase fluorination processes are known and are used in laboratory preparations, they have not received widespread acceptance for larger scale commercial use for various reasons. Heretofore, the most widely used catalyst for liquid phase fluorinations has been antimony pentachloride or a mixture of antimony pentachloride and antimony trichloride. However, antimony chlorides, although highly effective in the catalysis of many fluorination reactions, are very volatile materials. To avoid the problems associated with the volatility of antimony chlorides, such fluorination reactions are often carried out in closed systems under super-atmospheric pressure, necessitating the use of pressure equipment. In addition it has been found that to obtain desirably high yields, antimony chloride catalysts must be employed in relatively large concentrations. Thus, although antimony chlorides provide an effective catalyst for many fluorination reactions, a need exists for a still more effective catalyst that will overcome the aforementioned disadvantages.

A wide variety of other fluorination catalysts are known and have been used for various fluorination processes. However, the efficacy of a particular catalyst is highly specific and may depend on the nature of the reactants, that is the specific compound to be fluorinated and the particular fluorinating agent employed as well as the condition of the fluorination reaction, such as temperature, pressure, and physical phase of reactants.

It is an object of the present invention to provide an improved process for the liquid phase fluorination of organic halides. It is a further object to provide an improved catalyst for fluorination reactions that is relatively low in cost, of low volatility, and that may be effectively employed at relatively low concentrations. It is a further object to provide an improved process for the fluorination of organic halides in the liquid phase by reaction with hydrogen fluoride, wherein the hydrogen fluoride may be employed in either concentrated or dilute form. It is a still further object to provide a multi-step fluorination process comprising both a vapor phase and a liquid phase reaction wherein substantial improvements in the effective utilization of hydrogen fluoride reactant are achieved and the amount of hydrogen fluoride waste product is substantially reduced.

SUMMARY OF THE INVENTION

In accordance with the present invention, there is provided a process for the preparation of fluorinated aromatic compounds which comprises reacting a halomethyl aromatic compound, wherein the halo- is other than fluorine, with a fluorinating agent in the presence of a catalytic amount of a catalyst selected from the group consisting of pentachlorides and pentafluorides of tantalum, niobium and rhenium. The halomethyl aromatic compound may also contain stable ring constituents, such as halogen, alkyl, alkoxy, substituted alkyl and the like, or other substituents that will not adversely affect the reaction.

In particular, this invention is directed to a process for the preparation of compounds of the formula

which comprises contacting compounds of the formula

in the liquid phase, with hydrogen fluoride in the presence of a pentachloride or pentafluoride of tantalum, niobium and rhenium, wherein Ar is aryl;
R is a substituent on the aryl nucleus selected from the group consisting of aryl, substituted aryl, halogen, alkyl, alkoxy and substituted alkyl;
n is 1 to 9;
X is halogen atom other than fluorine;
w is 0 to 2;
p is 1 to 3;
w' is 1 to 3, and is greater than w;
p' is 0 to 2, and is less than p;
w + p is 3;
w' + p' is 3;
Z is 1–10; and
the maximum value of n + Z is 10.

Among the R substituents encompassed within the formula shown above, are alkyl radicals of from 1 to about 20 carbon atoms, and preferably of from 1 to about 12 carbon atoms, such as methyl, ethyl, propyl, butyl, amyl, octyl, decyl, dodecyl, pentadecyl, eicosyl, as well as their various isomer forms, such as isoproyl and isobutyl, said alkyl radical being a monovalent radical derivable from an aliphatic hydrocarbon alkane by the removal of 1 hydrogen atom; substituted alkyl of from 1 to about 30 carbon atoms and preferably of from 1 to about 15 carbon atoms, said alkyl group being substituted by one or more of aryl, substituted aryl, and the like; alkoxy and substituted alkoxy of from 1 to about 20 carbon atoms, and preferably of from 1 to about 12 carbon atoms, such as methoxy, ethoxy, propoxy, butoxy, pentoxy, octoxy, dodecoxy, pentadecoxy, eicosoxy, as well as their various isomer forms, such as iso-propoxy, iso-butoxy, and the like; and, halogen being chlorine, bromine, or iodine. Various other R substituents may be present on the haloalkyl aromatic compound reactants and corresponding products will be obtained. The number (n) of R substituents present on the aromatic nucleus is from 0 to 9 and preferably from 0 to 5. The number (Z) substituents on the aromatic nucleus is from 1 to 10 and preferably 1 or 2. The maximum number of substituents (n + Z) is equal to the total number of positions available on the aromatic nucleus. Thus when Ar is benzene, the maximum value of n + Z is 6, and in this instance if the value of n is 3, the maximum value of Z will be 3. Similarly when Ar is naphthalene, the maximum value of n + Z is 8 and when Ar is anthracene the maximum value of n + Z is 10.

The designation Ar or aryl represent an aromatic structure such as benzene, naphthalene, anthracene and the like, preferably of up to 14 carbon atoms. The preferred compounds prepared in accordance with this invention are those of the above formula wherein Ar is benzene, n is 0 to 5, Z is 1 to 6 and the maximum value of m + Z is 6.

In a preferred embodiment, the process of this invention is directed to the fluorination of compounds of the formula

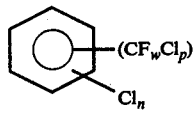

in the presence of a catalytic amount of a TaCl$_5$, NbCl$_5$, ReCl$_5$ or TaF$_5$ to prepare compounds of the formula

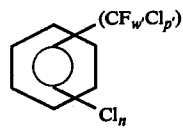

wherein
n is 0 to 2;
w is 0 to 2;
p is 1 to 3;
w' is 1 to 3, and is greater than w;
p' is 0 to 2, and is less than p;
w + P is 3; and
w' + p' is 3.

The most preferred compounds to be fluorinated in accordance with the invention are benzotrichloride, monochlorobenzotrichloride, and dichlorobenzotrichloride. The fluorination occurs on the side chain of the aromatic compound with the replacement of the halogen atoms thereof by fluorine. The decree of fluorination will depend in part on the amount of hydrogen fluoride supplied to the reaction and the length of time the reaction is carried out. Thus, for example, depending on these and other conditions of reactions described hereinbelow, the compound

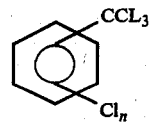

in the liquid phase, may be reacted with hydrogen fluoride, in the presence of pentachloride or pentafluoride of tantalum, niobium or rhenium to prepare

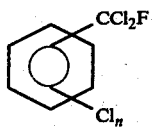 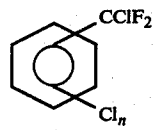 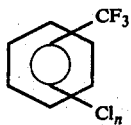

I  II  III or mixtures thereof. Alternatively, partially fluorinated compounds, such as compounds I and II may be employed as starting materials and further fluorinated by the process of this invention to produce higher fluorinated compounds such as compounds II and III.

The temperature of the reaction may vary considerably, but will typically be maintained in a range of about 0° C. to the boiling point of the halogenated aromatic reactant. The optimum temperature will vary somewhat, depending on the particular halogenated aromatic compound to be fluorinated. Preferably, in the fluorination of benzotrichloride, the reaction temperature is about 20° to about 75° C. The reactions are preferably carried out at atmospheric pressure, although sub-atmospheric or super-atmospheric pressures may be employed.

The amount of catalyst employed may vary considerably, for example, be utilized in amounts as high as 5 percent or higher based on the weight of reaction mixture. Higher concentrations may be employed but provide no special advantage and in addition, increase the possibility of polymer formation. Moreover, it is a particular advantage of the catalyst of this invention that the reaction may be effectively carried out with relatively low concentrations of catalyst. Thus, the preferred amount of catalyst is about 0.01 to about 1.0 percent by weight based on the amount of halogenated aromatic compound. Most preferably, the amount of catalyst is about 0.02 to about 0.2 percent by weight based on the amount of halogenated aromatic compound.

Typically, the process of this invention is carried out by charging the liquid halomethyl aromatic compound and catalyst to a reactor and feeding hydrogen fluoride in either the liquid or gaseous state, at a temperature, for example, of about 0° to about 100° C., into the charged reactor. The reaction mixture may be stirred or agitated to provide good contact of the reactants and the catalyst. The reaction may be carried out in a batch process or continuous process. The length of time of the reaction will vary considerably, depending for example, on the strength or concentration of the hydrogen fluoride employed and the degree of fluorination desired.

It is preferred to carry out the fluorination process of this invention in the absence of a solvent. However, a solvent may be employed, if desired. Typical solvents which may be employed include, for example, aromatic hydrocarbon solvents, such as benzene, or perfluorinated solvents, such as perfluorinated alkanes and the like, which solvents may, in some instances, be added as a reactant.

The amount of hydrogen fluoride employed will vary depending on the degree of fluorination desired. An excess may be employed. However, it is a particular advantage of the process of this invention that a large excess hydrogen fluoride is not required. Thus, hydrogen fluoride is preferably employed in an amount of approximately stoichiometric quantities, up to about 15 percent stoichiometric excess.

In one aspect of this invention, the liquid phase fluorination, utilizing a catalyst may be combined with a known vapor phase fluorination process to provide a highly effective two step fluorination process wherein improved utilization of hydrogen fluoride is achieved. Vapor phase fluorination processes commonly employ a substantial stoichiometric excess of hydrogen fluoride-typically in the range of a 50 percent excess. As a result, the off-gasses from such processes are a mixture of HF and HCl. Dilute HF mixtures of this type are generally ineffective as starting materials in the vapor phase processes and thus are not readily re-cyclable in the process. However, it is a particular advantage of this invention that hydrogen fluoride may be employed in either concentrated or dilute form, and in particular, in as a mixture of HF and HCl. Thus, the process of this invention provides an effective means of utilization of the dilute HF effluent gases of a vapor phase fluorination process.

HF-HCl mixtures, such as the effluent gases from a vapor phase fluorination process may be utilized as fluorinating agents in accordance with this invention either in a separate, independent liquid phase fluorination process or as an additional step, in combination with a vapor phase fluorination process. In the latter case, the HF-HCl off-gases from a vapor phase process may be supplied directly or indirectly to a liquid phase reactor charged with the catalyst and the haloalkyl aromatic compound to be fluorinated. The haloalkyl aromatic compound is then at least partially fluorinated in the manner hereindescribed so that for example on the average, at least one halogen atom on the haloalkyl side chain is replaced by a fluorine atom. The liquid phase fluorination may be carried out to various degrees of fluorination. Thus, in the liquid phase fluorination step, the haloalkyl aromatic may be fully fluorinated or fluorinated to the degree required for a particular product and this fully or partially fluorinated product recovered as the end product. Alternatively, in a preferred embodiment, the haloalkyl aromatic is partially fluorinated in the liquid phase and the partially fluorinated product re-cycled to the vapor phase fluorination step to be more fully fluorinated. As an example of this embodiment, the preparation of p-chlorobenzotrifluoride may be considered. In a simplified overview the process may be described as follows:

p-chlorobenzotrichloride is fed into a vapor phase fluorination reactor together with a substantial excess of anhydrous hydrogen fluoride and reacted therein until substantially complete conversion to p-chlorobenzofluoride is achieved. The effluent gas, primarily a mixture of HF and HCl is routed to a liquid phase reactor charged with p-chlorobenzotrichloride and a catalytic amount of a pentachloride or pentafluoride of niobium, tantalum or rhenium. In the liquid phase fluorination step the p-chlorobenzotrichloride is partially fluorinated to form, for example, a monofluorinated product and/or a difluorinated product. This partially fluorinated product is then filtered and recycled to the vapor phase reactor, and combined with the vapor phase starting material p-chlorobenzotrichloride to be substantially fully fluorinated by reaction with anhydrous HF. The preferred partially fluorinated product of the liquid phase reaction, to be recycled is the monofluorinated product. The final off-gas from this two step process is HCl which may contain minor amounts, such as up to about 10% of HF. The HF may be separated by known means to produce substantially pure HCl, useful in a variety of commercial purposes, such as the production of commercial grade muriatic acid.

The aforementioned "monofluorinated product" and "difluorinated product" refer to products having a corresponding average replacement of halogen atoms by fluorine atoms, even though some molecules may have no halogen atoms replaced while others may have one, two or three halogen atoms replaced. Thus, for example, in the fluorination of benzotrichloride, the monofluorinated product may be a mixture of benzotrichloride ($\alpha,\alpha,\alpha$-trichlorotoluene), benzofluorodichloride ($\alpha$-fluoro-$\alpha,\alpha$-dichlorotoluene), benzodifluorochloride ($\alpha,\alpha$-difluoro-$\alpha$-chlorotoluene) and benzotrifluoride ($\alpha,\alpha,\alpha$-trifluorotoluene) wherein the average replacement for all of the benzotrichloride molecules subject to the fluorination process is approximately one fluorine atom per molecule. In a similar manner, the difluorinated product may refer to a product wherein the average replacement is two fluorine atoms per molecule.

It will be seen that in accordance with the description hereinabove the liquid phase fluorination process of this invention may be employed in the production of partially fluorinated or fully fluorinated haloalkyl aromatic products (the term "fluorinated" referring to fluorine replacements on the haloalkyl side chain); and may utilize as the fluorinating agent either anhydrous HF or dilute HF-HCl mixtures or other fluorinating agents. Furthermore, this liquid phase process may be employed as an independent process or may be employed in a two step process together with a vapor phase fluorination step. One suitable vapor phase reaction that may be employed in combination with the liquid phase process of this invention is described in U.S. Pat. No. 3,859,372, the disclosure of which is incorporated herein by reference. However, other vapor phase processes known in the art may similarly be combined with the liquid phase process of this invention.

The examples set forth hereinbelow will serve to further illustrate the invention and the manner in which it may be practiced. The examples are set forth for purposes of illustration and are not to be construed as limitative of the present invention. Many variations of the process may be made without departing from the spirit and scope of the invention. In the examples, unless otherwise stated, all parts and percentages are by weight and all temperatures are in ° C.

EXAMPLE I

A Teflon ® reaction vessel, equipped with a reflux condenser, was charged with 586 parts of benzotrichloride and 10.75 parts of powdered $TaCl_5$ (0.01 moles $TaCl_5$/mole of benzotrichloride) was dispersed therein. The mixture was heated to about 55° C. and anhydrous hydrogen fluoride, pre-heated to about 55° C., was bubbled in at a rate of about 1.2 parts/minute, with continuous agitation, for a period of 166 minutes. Completion of the reaction was indicated when HCl evolution ceased and HF began to reflux and the reaction temperature dropped. The organic product was treated with sodium carbonate and filtered. Analysis of the product by gas chromatographic techniques indicated 94.0% benzotrifluoride (BTF) and 4.0% benzodifluorochloride. Overall degree of fluorination was 96.0% and HF utilization was 84%.

EXAMPLE 2

A mixture of 586 parts of benzotrichloride and 8.11 parts of $NbCl_5$ (0.01 moles $NbCl_5$/mole of benzotrichloride) was heated to about 55° C. and maintained thereat while anhydrous hydrogen fluoride, preheated to about 55° C. was bubbled into the mixture at a rate of about 1.08 parts per minute, with continuous agitation for a period of about 195 minutes. The reaction product was treated with sodium carbonate, filtered, and analyzed by gas chromatography. The product comprises 95.5 percent benzotrifluoride (BTF), 0.2 percent benzodiflurorochloride and about 3.6 percent of higher boiling materials. Overall degree of fluorination was 95.6 percent. HF utilization was 81 percent.

EXAMPLE 3

A mixture of 586 parts of benzotrichloride and 2.18 parts of $ReCl_5$ (0.002 moles of $ReCl_5$/mole of benzotrichloride) was heated and maintained at a temperature of about 55° C. with continuous agitation while anhydrous hydrogen fluoride was bubbled in at a rate of about 1.29 parts per minute for a period of about 187 minutes. The reaction product was treated with sodium carbonate and filtered. Analysis of the product by gas chromatography techniques indicated 78.5 percent benzotrifluoride (BTF) and 21.2 percent benzodifluorochloride. HF utilization was 69 percent and the degree of fluorination was 92.6 percent.

EXAMPLE 4

A mixture of 586 parts of benzotrichloride and 8.27 parts of $TaF_5$ was heated to about 55° to 60° C. and maintained thereat while anhydrous hydrogen fluoride, preheated to about 55° C. was bubbled into the mixture at a rate of about 1.0 parts per minute, with continuous agitation for a period of about 192 minutes. The reaction product was treated with sodium carbonate, filtered, and analyzed by gas chromatography. The product comprises 94.2 percent benzotrifluoride (BTF), 0.7 percent benzodifluorochloride, and about 0.5 percent orthochlorobenzotrifluoride, 4.6 percent of higher boiling materials. HF utilization was 85 percent.

EXAMPLES 5–27

Following the procedure of Examples 1–3, benzotrichloride (BTC) was fluorinated in a series of experiments using various Lewis acid catalysts. The results are set forth in Table I below. In each instance, 586 parts of benzotrichloride was employed and the amounts of catalyst and HF, and conditions of reaction were varied, as shown. In the table, those examples designated "C" (following the example number), are provided for purposes of comparison.

TABLE I

| Example No. | Catalyst | Percent Weight of Catalyst | Reactor Temp. (° C) | HF Flow Rate (parts/min.) | Reaction Time (min.) | Total HF (parts/min.) | Products (%) | | | |
|---|---|---|---|---|---|---|---|---|---|---|
| | | | | | | | BTF | Benzo difluoro-chloride | Benzo-fluoro-dichloride | High Boiling material |
| 5 | $TaCl_5$ | 0.18 | 55 – 58 | 2.4 | 79 | 190 | 37.6 | 61.6 | 0.3 | 0.1 |
| 6 | " | 0.18 | 54 – 59 | 2.4 | 102 | 245 | 84.6 | 15.2 | — | 0.2 |
| 7 | " | 0.18 | 55 – 59 | 1.4 | 166 | 204 | 94.0 | 3.8 | — | 1.3 |
| 8 | $NbCl_5$ | 0.1 | 55 – 57 | 2.4 | 97 | 234 | 33.2 | 65.3 | 0.6 | 0.5 |
| 9 | " | 0.2 | 53 – 57 | 2.8 | 97 | 250 | 66.2 | 33.1 | — | — |
| 10 | " | 0.5 | 48 – 52 | 2.4 | 98 | 228 | 77.2 | 21.4 | 0.1 | 1.0 |
| 11 | " | 1.0 | 50 – 56 | 2.4 | 94 | 226 | 88.2 | 9.6 | — | 1.7 |
| 12 | " | 2.7 | 55 – 61 | 2.4 | 92 | 221 | 91.4 | 7.4 | 0.1 | 0.7 |
| 13 | " | 2.7 | 59 – 61 | 1.4 | 151 | 211 | 92.7 | 1.3 | — | 5.7 |
| 14 | " | 1.4 | 66 – 72 | 1.4 | 195 | 212 | 95.5 | 0.2 | — | 3.6 |
| 15 | $ReCl_5$ | 0.19 | 57 – 59 | 1.35 | 203 | 270 | 60.1 | 39.8 | — | — |
| 16 | " | 0.37 | 56 – 60 | 1.29 | 190 | 241 | 78.5 | 21.2 | — | 0.1 |
| 17C | $AlCl_3$ | 0.1 | 30 – 55 | 2.4 | 80 | 193 | 0.5 | 3.2 | 69.4 | — |
| 18C | " | 0.7 | 55 – 57 | 2.4 | 95 | 248 | 9.8 | 53.7 | 36.0 | 0.2 |
| 19C | " | 3.3 | 50 – 53 | 1.4 | 196 | 284 | 76.4 | 22.1 | 0.1 | 1.1 |
| 20C | $FeCl_3$ | 0.8 | 56 – 58 | 0.7 | 180 | 188 | 68.6 | 24.7 | — | 6.5 |
| 21C | $WCl_6$ | 0.2 | 57 – 58 | 0.7 | 239 | 163 | 3.5 | 84.3 | 12.1 | 0.1 |
| 22C | " | 1.0 | 55 – 57 | 0.7 | 252 | 163 | 24.6 | 75.2 | — | 0.2 |
| 23C | $TiCl_3$ | 0.8 | 50 – 54 | 0.7 | 301 | 202 | 8.5 | 69.4 | 21.6 | — |
| 24C | $TiCl_4$ | 1.0 | 50 – 54 | 0.64 | 331 | 213 | 33.9 | 65.1 | 0.8 | 0.2 |
| 25C | $SnCl_4$ | 1.3 | 50 – 55 | 0.67 | 322 | 217 | 2.8 | 75.4 | 21.6 | 0.03 |
| 26C | $PCl_5$ | 0.1 | 54 – 33 | 2.4 | 80 | 189 | 0 | 1.43 | 75.01 | — |
| 27C | None | 0 | 54 – 56 | 0.67 | 308 | 206 | 0.08 | 3.02 | 81.8 | — |

What is claimed is:

1. A process for the preparation of compounds of the formula

comprising contacting compounds of the formula

in liquid phase, with hydrogen fluoride in the presence of a catalyst selected from the group consisting of pentachlorides and pentafluorides of tantalum, niobium and rhenium wherein Ar is aryl;
R is a substituent on the aryl nucleus selected from the group consisting of aryl, substituted aryl, halogen, alkyl, alkoxy, and substituted alkyl;
n is 0 to 9;
X is a halogen atom other than fluorine;
w is 0 to 2;
p is 1 to 3;
w' is 1 to 3, and is greater than w;
p' is 0 to 2, and is less than p'
w + p is 3;
w' + p' is 3;

Z is 1–10; and the maximum value of n + Z is 10.

2. A process according to claim 1 wherein Ar is benzene, n is 0 to 5, Z is 1–6, and the maximum value of n + Z is 6.

3. A process according to claim 2 wherein R is chlorine, and n is 0 to 2.

4. A process according to claim 3 wherein X is chlorine.

5. A process according to claim 4 wherein Z is 1.

6. A process according to claim 5 wherein p is 3 and w is 0.

7. A process according to claim 6 wherein n is 0.

8. A process according to claim 7 wherein p' is 0 and w' is 3.

9. A process according to claim 7 wherein p' is 1 and w' is 2.

10. A process according to claim 7 wherein p' is 2 and w' is 1.

11. A process according to claim 6 wherein n is 1.

12. A process according to claim 11 wherein p' is 0 and w' is 3.

13. A process according to claim 11 wherein p' is 1 and w' is 2.

14. A process according to claim 11 wherein p' is 2 and w' is 1.

15. A process for the preparation of compounds of the formula

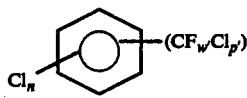

comprising contacting compounds of the formula

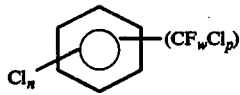

In the liquid phase, with hydrogen fluoride in the presence of tantalum pentachloride wherein
n is 0 to 2;
w is 0 to 2;
p is 1 to 3;
w' is 1 to 3, and is greater than w;
p' is 0 to 2, and is less than p;
w + p is 3 and
w' + p' is 3.

16. A process according to claim 15 for the preparation of benzotrifluoride which comprises contacting benzotrichloride with hydrogen fluoride in the presence of a catalytic amount of tantalum pentachloride.

17. A process for the preparation of compounds of the formula

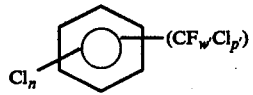

comprising contacting compounds of the formula

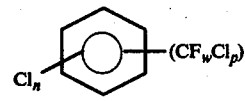

in the liquid phase, with hydrogen fluoride in the presence of niobium pentachloride wherein n is 0 to 2;
w is 0 to 2;
p is 1 to 3;
w' is 1 to 3, and is greater than w;
p' is 0 to 2, and is less than p;
w + p is 3 and
w' + p' is 3.

18. A process according to claim 17 for the preparation of benzotrifluoride which comprises contacting benzotrichloride with hydrogen fluoride in the presence of a catalytic amount of niobium pentachloride.

19. A process for the preparation of compounds of the formula

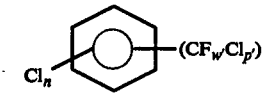

comprising contacting compounds of the formula

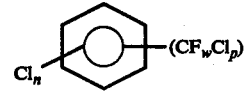

in the liquid phase, with hydrogen fluoride in the presence of rhenium pentachloride wherein n is 0 to 2;
w is 0 to 2;
p is 1 to 3;
w' is 1 to 3, and is greater than w;
p' is 0 to 2, and is less than p;
w + P is 3 and
w' + p' is 3.

20. A process according to claim 19 for the preparation of benzotrifluoride which comprises contacting benzotrichloride with hydrogen fluoride in the presence of a catalytic amount of rhenium pentachloride.

21. A process for the preparation of compounds of the formula

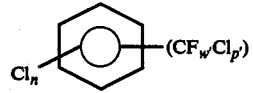

comprising contacting compounds of the formula

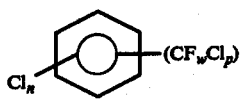

in the liquid phase, with hydrogen fluoride in the presence of tantalum pentafluoride wherein n is 0 to 2;
w is 0 to 2;
p is 1 to 3;
w' is 1 to 3, and is greater than w;
p' is 0 to 2, and is less than p;
w + p is 3 and
w' + p' is 3.

22. A process according to claim 21 for the preparation of benzotrifluoride which comprises contacting benzotrichloride with hydrogen fluoride in the presence of a catalytic amount of tantalum pentafluoride.

* * * * *